United States Patent [19]

Schweizer

[11] Patent Number: 4,591,597
[45] Date of Patent: May 27, 1986

[54] ANTIDIABETIC IMINOSULPHONAMIDES

[75] Inventor: Ernst Schweizer, Arlesheim, Switzerland

[73] Assignee: Ciba-Geigy Corporation, Ardsley, N.Y.

[21] Appl. No.: 594,148

[22] Filed: Mar. 28, 1984

[30] Foreign Application Priority Data

Apr. 5, 1983 [CH] Switzerland ............... 1817/83

[51] Int. Cl.$^4$ ............... A61K 31/415; C07D 233/46
[52] U.S. Cl. ............... 514/392; 548/315
[58] Field of Search ............... 548/315; 424/273 R; 514/392

[56] References Cited

U.S. PATENT DOCUMENTS 3,812,144  5/1974  Dietrich et al. ............... 548/315

FOREIGN PATENT DOCUMENTS 510031  8/1971  Switzerland ............... 548/315
542214  11/1973  Switzerland ............... 548/315

OTHER PUBLICATIONS

*Chemical Abstracts*, 76:14542j (1972) [Swiss 510,031, Dietrich et al., 8/31/71].
*Chemical Abstracts*, 80:47990q (1974) [Swiss 542,214, Dietrich et al., 11/15/73].

E. H. Schweizer et al. *J. Med. Chem.*, vol. 26, pp. 964–970 (Jul. 1983).

*Primary Examiner*—Richard A. Schwartz
*Attorney, Agent, or Firm*—Michael W. Glynn; Irving M. Fishman

[57] ABSTRACT

The compounds of the formula

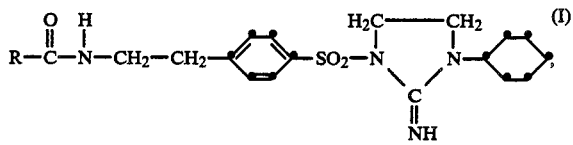

in which R represents the radical of the formula

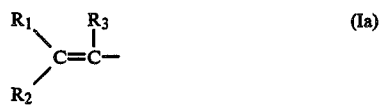

in which
$R_1$ represents lower alkyl and
each of $R_2$ and $R_3$, independently of the other, represents hydrogen or lower alkyl,
and salts thereof exhibit antidiabetic actions.

9 Claims, No Drawings

ANTIDIABETIC IMINOSULPHONAMIDES

The present invention relates to iminosulphonamides and processes for the manufacture thereof, pharmaceutical preparations containing such iminosulphonamides, and the use of these iminosulphonamides as pharmacologically active compounds.

The invention relates especially to 1-{4-[2-(acylamino)-ethyl]-phenylsulphonyl}-3-cyclohexyl-2-imino-imidazolidine compounds of the formula

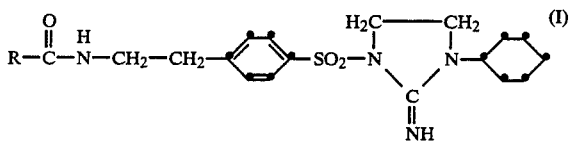

in which R represents the radical of the formula

in which
R$_1$ represents lower alkyl and
each of R$_2$ and R$_3$, independently of the other, represents hydrogen or lower alkyl,
and salts of such compounds.

Lower alkyl has preferably up to and including 3 carbon atoms, lower alkyl groups R$_2$ and R$_3$ representing especially methyl, whilst R$_1$ may represent, for example, methyl, ethyl, n-propyl or isopropyl.

With regard to R$_1$ and the carbonyl group, the compounds of the formula I may have the cis- but preferably have the trans-configuration.

The novel compounds may be in the form of acid addition salts, especially in the form of pharmaceutically acceptable, non-toxic acid addition salts. Suitable salts are, for example, those with inorganic acids, such as hydrochloric acid, hydrobromic acid, sulphuric acid or phosphoric acid, or with organic acids, such as aliphatic, cycloaliphatic, aromatic or heterocyclic carboxylic or sulphonic acids, for example formic acid, acetic acid, propionic acid, succinic acid, glycolic acid, lactic acid, malic acid, tartaric acid, citric acid, maleic acid, hydroxymaleic acid, pyruvic acid, fumaric acid, benzoic acid, 4-aminobenzoic acid, anthranilic acid, 4-hydroxybenzoic acid, salicyclic acid, embonic acid, methanesulphonic acid, ethanesulphonic acid, 2-hydroxyethanesulphonic acid, ethylenesulphonic acid, toluenesulphonic acid, naphthalenesulphonic acid or sulphanilic acid, or with other acidic organic compounds, such as ascorbic acid.

The present invention relates especially to compounds of the formula I in which R represents the radical of the formula Ia, and R$_1$ represents alkyl having up to and including 3 carbon atoms, R$_2$ represents preferably hydrogen, and also methyl, and R$_3$ represents hydrogen or methyl, it being possible for these compounds to have the cis- or, preferably, the trans-configuration with regard to the radical R$_1$ and the carbonyl group, and especially to 3-cyclohexyl-2-imino-1-{4-[2-(crotonylamino)-ethyl]-phenylsulphonyl}imidazolidine (trans), and salts, especially pharmaceutically acceptable salts, thereof.

The novel compounds of the present invention can be obtained in a manner known per se, for example (a) by reacting a compound of the formula

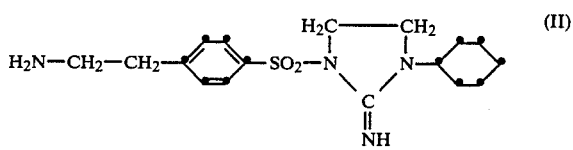

or a derivative thereof with an acid of the formula R—C(=O)—OH (III) or a reactive derivative, and, if desired, converting a salt obtainable according to the invention into the free compound or into a different salt, and/or converting a free compound obtainable according to the invention into a salt and/or, if desired, separating a mixture of isomers into the individual isomers.

A derivative of the starting material of the formula II may be, for example, a silyl derivative, such as a tri-lower alkylsilyl, such as trimethylsilyl, derivative, and also an acid addition salt, such as a salt with one of the acids mentioned hereinbefore.

A reactive derivative of an acid of the formula III is especially an anhydride, including an asymmetric anhydride, such as, inter alia, an anhydride with a strong inorganic acid, such as a hydrohalic acid especially the corresponding acid chloride, or with a carbonic acid semiester, such as a carbonic acid lower alkyl semiester, for example carbonic acid isopropyl semiester, or an internal anhydride, that is to say the corresponding ketene compound. Suitable reactive acid derivatives are also esters, such as a lower alkyl ester, for example methyl or ethyl ester, and especially, however, activated esters of acids of the formula III, such as suitably substituted phenyl esters, for example 4-nitrophenyl ester or pentachlorophenyl ester, or suitably substituted methyl esters, for example cyanommethyl ester.

The reaction can be carried out in a manner known per se, if necessary in the presence of a condensation agent, for example a carbodiimide, such as N,N'-dicyclohexyl-carbodiimide, these being employed especially when a free acid of the formula III is used, or an acid-binding agent, such as, for example, an inorganic base or salt, such as an alkali metal hydroxide, alkali metal bicarbonate, alkali metal carbonate or alkali metal phosphate, such as the corresponding sodium or potassium compound. It is also possible to use an organic base, for example pyridine, trimethylamine, triethylamine, N,N-diisopropylethylamine or collidine, which, when added in excess, can be used at the same time also as solvent. The reaction is usually carried out in the presence of a solvent, preferably an inert organic solvent which may or may not be miscible with water, in the presence or absence of water. Suitable inert organic solvents are, for example, hydrocarbons, such as benzene, toluene or xylene, ethers, such as diethyl ether, dioxan or tetrahydrofuran, halogenated hydrocarbons, such as methylene chloride, or lower ketones, such as acetone or methyl ethyl ketone. The reaction may, if necessary, be carried out while cooling or heating, under elevated pressure and/or in an inert gas atmosphere, such as a nitrogen atmosphere.

The starting materials of the formulae II and III are known; those of the formula II can be obtained, for example, by treating an acid addition salt, such as the hydrochloride of 4-(2-aminoalkyl)-phenylsulphonamide, with N-(2-chloroethyl)-N-cyclohexyl-cyanamide in the presence of an alkali metal hydroxide, for example potassium hydroxide.

The novel compounds of the formula I can also be obtained if (b) a reactive derivative of a sulphonic acid of the formula

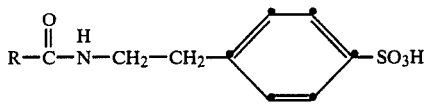

is reacted with a compound of the formula

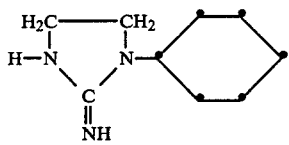

or a derivative thereof, and, if desired, the additional process steps are carried out.

Reactive derivatives of sulphonic acids of the formula IV are especially the anhydrides thereof, especially mixed anhydrides with strong acids, such as hydrophalic acids, especially the corresponding chlorides, and also the corresponding symmetric anhydrides.

A derivative of a compound of the formula V may be, for example, a silyl derivative, such as a tri-lower alkylsilyl, such as trimethylsilyl, derivative, and also an acid addition salt, such as a salt with one of the acids mentioned hereinbefore.

The reaction can be carried out in a manner known per se, if necessary in the presence of an acid-binding agent, such as, for example, an inorganic base or salt, such as an alkali metal hydroxide, alkali metal bicarbonate, alkali metal carbonate or alkali metal phosphate, such as the corresponding sodium or potassium compound. It is also possible to use an organic base, for example pyridine, trimethylamine, triethylamine, N,N-diisopropylethylamine or collidine, which, when added in excess, can be used at the same time also as solvent. The reaction is usually carried out in the presence of a solvent, preferably an inert organic solvent which may or may not be miscible with water, in the absence or presence of water. Suitable inert organic solvents are, for example, hydrocarbons, such as benzene, toluene or xylene, ethers, such as diethyl ether, dioxan or tetrahydrofuran, halogenated hydrocarbons, such as methylene chloride, or lower ketones, such as acetone or methyl ethyl ketone. The reaction may, if necessary, be carried out while cooling or heating, under elevated pressure and/or in an inert gas atmosphere, such as a nitrogen atmosphere.

The starting materials are known or can be manufactured in a manner known per se, it being possible to obtain, for example, halides of acid compounds of the formula IV, for example by treating a N—R—C(=O)-2-phenylethylamine with a halosulphonic acid, especially chlorosulphonic acid.

The novel compounds of the formula I can also be obtained by (c) cyclising a compound of the formula

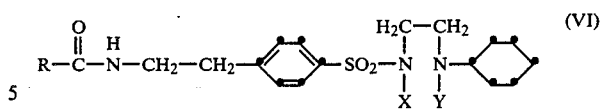

in which one of the radicals X and Y represents cyano and the other represents hydrogen, and, if desired, carrying out the additional process steps.

The cyclisation mentioned above can be carried out under reaction conditions that are known per se. In so doing, the starting material of the formula VI is usually formed in situ and, without being isolated, is converted directly into a compound of the formula I.

Thus, for example (ca) a compound of the formula

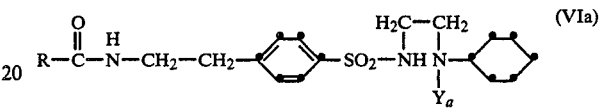

in which $Y_a$ represents hydrogen or a radical that can be removed under the reaction conditions, can be reacted with a reactive derivative of cyanic acid; in this manner, it is possible to obtain a compound of the formula I directly without isolating an intermediate of the formula VI.

In a starting material of the formula VIa, for example a radical that can be removed under the reaction conditions, that is to say upon reaction with the cyanic acid derivative, is a methyl group which is optionally mono-, di- or tri-substituted, for example by an aryl group, such as phenyl optionally substituted, for example, by lower alkyl, such as methyl, lower alkoxy, such as methoxy, or halogen, such as chlorine, or a methyl group which is optionally substituted by lower alkenyl, such as vinyl, that is unsaturated at the linking carbon atom.

A reactive derivative of cyanic acid is, for example, a halide, such as cyanogen chloride or cyanogen bromide, or an ester, such as a lower alkyl ester or, especially, a phenyl ester thereof.

The reaction can be carried out in a manner known per se, if necessary in the presence of an acid-binding agent, such as an inorganic base, for example an alkali metal hydroxide, bicarbonate, carbonate or phosphate, such as the corresponding sodium or potassium compound. Calcium carbonate, and also calcium phosphate or magnesium carbonate may also be used.

The reaction is effected in the absence, but preferably in the presence, of an inert, usually organic solvent, if desired in the presence of water. Suitable solvents are, for example, hydrocarbons, such as benzene, toluene or xylene, lower alkanols, such as methanol or ethanol, ethers, such as diethyl ether, dioxan or tetrahydrofuran, halogenated hydrocarbons, such as methylene chloride, lower ketones, such as acetone or methyl ethyl ketone, carboxylic acid esters, such as ethyl acetate, carboxylic acid nitriles, such as acetonitrile, or sulphones, such as tetrahydrothiophene 1,1-dioxide. The reaction is carried out, if necessary, while cooling or heating, under elevated pressure and/or in an inert gas atmosphere, such as a nitrogen atmosphere.

A starting material of the formula VIa can be obtained, for example, by treating a 4-[2-(R-carbonylamino)-ethyl]-benzenesulphonyl chloride with aziridine and reacting the resulting N-{4-[2-(R-carbonylamino)-ethyl]-phenylsulphonyl}-aziridine with a N-$Y_a$-cylcohexylamine.

It is also possible (cb) to react a compound of the formula

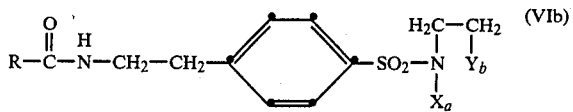

in which $X_a$ represents hydrogen and $Y_b$ represents a reactive esterified hydroxy group, or in which $X_a$ and $Y_b$ together form a bond, with N-cyclohexyl-cyanamide or a derivative thereof; in this manner, compounds of the formula I can be obtained directly without isolating an intermediate of the formula VI.

A reactive esterified hydroxy group $Y_b$ is hydroxy esterified by a strong inorganic or organic acid, such as a hydrohalic acid, for example hydrochloric acid or hydrobromic acid, or an organic sulphonic acid, such a p-toluenesulphonic acid or methanesulphonic acid.

A derivative of N-cyclohexyl-cyanamide is especially a metal derivative, such as an alkali metal, for example lithium, sodium or potassium, derivative, or an alkaline earth metal, for example calcium, derivative. Such a derivative is used especially in the reaction with a starting material of the formula IIb in which $X_a$ and $Y_b$ together form a bond.

The reaction can be carried out in a manner known per se and, when using starting materials of the formula VIb in which $X_a$ represents hydrogen and $Y_b$ represents a reactive esterified hydroxy group, preferably in the presence of acid-binding agents, such as inorganic or organic bases, for example alkali metal or alkaline earth metal hydroxides, such as sodium or potassium hydroxide. If necessary or desired, the reaction is carried out in the presence of a solvent, such as an ether, for example diethyl ether, tetrahydrofuran, dioxan, anisole or ethylene glycol dimethyl ether, or a lower alkanol, for example butanol, a carboxylic acid amide, such as dimethylformamide, or a sulphoxide, such as dimethyl sulphoxide, while cooling or heating, in a closed vessel and/or in an inert gas atmosphere, such as a nitrogen atmosphere.

The starting materials of the formula VIb can be obtained, for example, if a 4-[2-(R-carbonylamino)-ethyl]-benzenesulphonyl chloride is reacted with aziridine or with an acid addition salt of a 2-$Y_b$-ethylamine in which $Y_b$ represents a reactive esterified hydroxy group, preferably in the presence of a base, such as an alkali metal, for example sodium or potassium, hydroxide.

It is also possible (cc) to react a compound of the formula

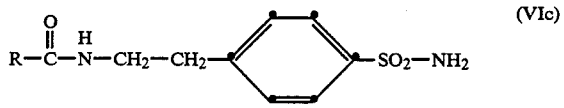

with a reactive esterified N-cyclohexyl-N-(2-hydroxyethyl)-cyanamide or a derivative thereof; in this manner, compounds of the formula I can be obtained directly without isolating an intermediate of the formula VI.

In a reactive ester of N-(2-hydroxyethyl)-cyanamide, the hydroxy group is esterified by a strong inorganic or organic acid, such as a hydrohalic acid, for example hydrochloric acid or hydrobromic acid, or an organic sulphonic acid, such as p-toluenesulphonic acid or methanesulphonic acid.

A derivative of the cyanamide starting material is, for example, an acid addition salt, for example with a mineral acid, such as a hydrohalic acid, for example hydrochloric acid.

The reaction is carried out in a manner known per se, advantageously in the presence of an acid-binding agent, such as an inorganic base, for example an alkali metal hydroxide, bicarbonate, carbonate or phosphate, such as sodium or potassium hydroxide, bicarbonate, carbonate or phosphate, or also an organic base, such as a tertiary amine, for example N,N-diisopropylethylamine. If necessary or desired, the reaction is carried out in the presence of a suitable solvent, optionally in the presence of water, such as a lower alkanol, for example butanol, an ether, for example dioxan or diethylene glycol monomethyl ether, a carboxylic acid amide, for example N,N-dimethylformamide, or a sulphoxide, for example dimethyl sulphoxide, while cooling or heating, in a closed vessel and/or in an inert gas atmosphere, such as a nitrogen atmosphere.

The starting materials of the formula VIc can be obtained in a manner known per se, for example by aminolysis of a 4-[2-(R-carbonylamino)-ethyl]-benzenesulphonyl chloride or by treating 1-cyclohexylaziridine with a reactive derivative of cyanic acid, such as a cyanogen halide, for example cyanogen bromide.

A further process varient consists in (cd) cyclising an addition salt compound of the formula

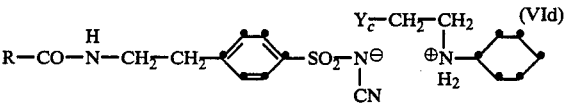

in which $Y_c$ represents a reactive esterified hydroxy group; in this manner, compounds of the formula I can be obtained directly without isolating an intermediate of the formula VI.

A reactive esterified hydroxy group $Y_c$ is especially halogen, especially bromine, and also chlorine, but may also be an organic sulphonyloxy group, such as methylsulphonyloxy or 4-methylphenylsulphonyloxy.

The reaction is carried out in a manner known per se, preferably while heating and, if necessary or desired, in the presence of a solvent, especially one of high boiling point, such as an ether, for example diethylene glycol dimethyl ether, or a carboxylic acid amide, for example N,N-dimethylformamide, in a closed vessel and/or in an inert gas atmosphere, for example a nitrogen atmosphere.

The starting material of the formula VId can be obtained, for example, if a 4-[2-(R-carbonylamino)-ethyl]-benzenesulphonyl chloride is reacted, for example by being treated with disodium cyanamide in water, to form a sodium derivative of the corresponding N-cyanobenzenesulphonamide and this is treated with a N-(2-$Y_c$-ethyl)-cyclohexylamine.

The novel compounds of the formula I can also be obtained if (d) a compound of the formula

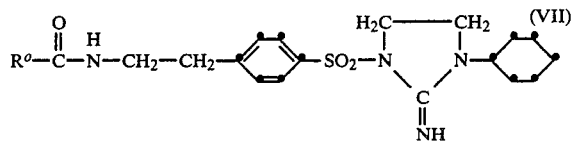

in which R° represents a radical of the formula

in which $R_1°$ represents a 1-lower alkenyl radical, or a derivative thereof is isomerized and, if desired, the additional process steps are carried out.

A derivative of a compound of the formula VII is especialy an acid addition salt, such as a salt with a mineral acid, such as a hydrohalic acid.

The isomerisation reaction usually occurs spontaneously, that is to say in situ in connection with the manufacture of the starting materials of the formula VII, if necessary or desired while heating and in the presence of a suitable solvent, in a closed vessel and/or in an inert gas atmosphere, for example a nitrogen atmosphere.

The starting materials can be obtained in a manner known per se, for example by treating a compound of the formula II with an acid of the formula $R°$—C(-=O)—OH (VIII) or a suitable derivative, for example an anhydride, such as a halide, for example the chloride, thereof, if necessary in the presence of a condensation agent or an acid-binding agent. As mentioned above, the starting material of the formula VII may isomerise spontaneously to a compound of the formula I.

Salts that are obtainable in accordance with the process can be converted in a manner known per se, for example by treatment with a suitable base, into the free compounds, or, for example by salt-exchange with a suitable salt, into a different salt.

Free compounds of the formula I that are obtainable according to the invention may, if desired, be converted into their acid addition salts, for example by reaction with an acid in a suitable solvent.

Mixtures of isomers that are obtainable according to the invention can be separated into the individual isomers in a manner known per se, for example by means of physico-chemical separating methods, with preferably the more active isomer being isolated.

The invention relates also to those forms of the process according to which a compound obtainable as intermediate at any stage of the process is used as starting material and the remaining steps are carried out or a starting material is used in the form of a derivative, for example a salt, and/or in the form of an isomer or mixture of isomers, or, as demonstrated above, is formed under the reaction conditions.

In the process of the present invention, the starting materials used are preferably those which result in the compounds mentioned at the beginning as being especially valuable. The present invention relates also to novel starting materials and to processes for the manufacture thereof.

The compounds of the present invention have pharmacological, and, especially, pronounced blood sugar-reducing, properties which can be demonstrated both in normal and in diabetic experimental animals.

The blood sugar-reducing action in normal experimental animals is determined in normal female rats (Tif: RAIF (SPF)) weighing from 170 to 200 g whose food was withdrawn 6.5 hours before the beginning of the test. After taking a first blood sample (starting value), the test preparation is administered orally (by means of a pharyngeal probe) in the form of a suspension in a 0.5% aqueous solution of methylcellulose and in a volume of 5 ml/kg body weight. Further samples of blood are taken after 2, 4.5 and 7.5 hours, at least 5 experimental animals being used per dose. The blood sample is taken retro-orbitally (Riley, Proc.Soc.Exptl. Biol. Med., vol. 104, page 751 (1960) under light anaesthetic (oxygen/carbon dioxide 1:1, 45 seconds; Green, Animal Handbooks 8, London Laboratory Animals Ltd., page 154 (1979)). The blood sugar is determined according to the enzymatic GOD method (Werner et al., Z. anal. Chem., vol. 252, page 224 (1970)) on an autoanalyser.

In this test procedure, the compounds of the present invention exhibit the following blood sugar-reducing actions:

| compound | maximum blood sugar reduction (as % of the starting value) in the doses indicated (in mg/kg p.o.) | | | |
|---|---|---|---|---|
| (Example) | 30 | 10 | 3 | 1 |
| 1 | 80 | 76 | 41 | 17 |
| 10 | — | 43 | 23 | 11 |
| 11 | 80 | 59 | 31 | 14 |
| 12 | 64 | 48 | 12 | — |
| 13 | 79 | 51 | 11 | — |

The blood sugar-reducing action in diabetic experimental animals is determined in streptozotocin-diabetic rats, the streptozotocin-diabetes being induced by a single injection of streptozotocin (55 mg/kg) into the caudal vein in male rats (Tif: RAIF (SPF)) weighing from 140 to 200 g whose food is withdrawn 16 to 24 hours before the beginning of the test. Experimental animals having blood sugar values of between 300 and 700 mg/percent (approximately 17 to 39 mmol/liter) are used for the tests 3 to 4 weeks, at the earliest, after this treatment.

The blood sugar is determined 3 to 6 hours after the oral administration of the test preparation (see above for normal rats) to animals that have been fed. Since the blood sugar in diabetic rats, in contrast to normal rats, decreases as a rule by 5 to 15% during the test period, the spontaneous blood sugar reduction (as % of the starting value) of a simultaneously investigated control group is deducted from the blood sugar reduction of the test group. At least 5 animals per group are used.

In this test procedure, the compound of Example 1, for example, exhibits, at a dosage of 100 mg/kg, a maximum blood sugar reduction (as % of the starting value) of 29% and, at a dosage of 30 mg/kg, one of 10%.

In addition, the compounds of the present invention have a low toxicity in comparison with the strong antidiabetic actions. Thus, for example, the $LD_{50}$ dose for the compound of Example 1 is 600 mg/kg p.o. (rat).

The compounds of the present invention can therefore be used for reducing the blood sugar level in diabetes, being suitable, by virtue of the rapid onset of action and the remarkably short duration of action (the maximum action is achieved, for example at a dosage of 2 mg/kg of the compound of Example 1, after 1 hour and the action can no longer be detected after 5 hours), especially for the periprandial treatment of diabetes of old age.

The invention relates also to the use of the compounds of the formula I or of pharmaceutically acceptable salts of such compounds having salt-forming properties, especially as pharmacologically active, particularly as blood sugar-reducing, compounds. They can be used, preferably in the form of pharmaceutical preparations, in a method for the prophylactic and/or therapeutic treatment of the animal or human body, especially for the treatment of diabetes. The dosage of the active ingredient which is administered on its own or together with the customary carrier and adjunct depends on the species to be treated, the age and individual condition thereof and also on the mode of administration. The daily dosages for mammals weighing approximately 70 kg is, depending on the type of diabetes, individual condition and age, preferably approximately from 50 to 500 mg.

The invention relates further to pharmaceutical preparations containing as active ingredients compounds of the formula I or pharmaceutically acceptable salts thereof, and to processes for the manufacture thereof.

The pharmaceutical preparations according to the invention are for enteral, such as peroral or rectal, and for sublingual administration and also for parenteral administration to warm-blooded animals. Corresponding unit dosage forms, especially for peroral and/or sublingual administration, for example dragées, tablets or capsules, contain preferably from approximately 50 to approximately 250 mg, especially from approximately 50 to approximately 150 mg, of a compound of the formula I or a pharmaceutically acceptable salt thereof together with pharmaceutically acceptable carriers.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes, using, for example, corn, wheat, rice or potato starch, gelatine, tragacanth or methylcellulose, and/or, if desired, disintegrators, such as the above-mentioned starches, also carboxymethyl starch, crosslinked polyvinylpyrrolidone, agar, alginic acid or a salt thereof, such as sodium alginate. Adjuncts are especially flow-regulating agents and lubricants, for example silica, talc, stearic acid or salts thereof, such as magnesium or calcium stearate, and/or polyethylene glycol.

Dragée cores can be provided with suitable coatings that may be resistant to gastric juice, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures, or, for the preparation of coatings that are resistant to gastric juice, solutions of suitable cellulose preparations, such as acetylcellulose phthalate or hydroxypropylmethylcellulose phthalate.

Dyes or pigments can be added to the tablets or dragée coatings, for example for identification purposes or to indicate different doses of active ingredient.

Other orally administerable pharmaceutical preparations are dry-filled capsules made from gelatine, and also soft, sealed capsules made from gelatine and a plasticiser, such as glycerine or sorbitol. The dry-filled capsules may contain the active ingredient in the form of granules, for example in admixture with fillers, such as lactose, binders, such as starches, and/or glidants, such as talc or magnesium stearate, and, optionally, stabilisers. In soft capsules, the active ingredient is preferably dissolved or suspended in suitable liquids, such as oils, paraffin oil or liquid polyethylene glycols, it being possible also to add stabilisers.

As rectally administerable pharmaceutical preparations there come into consideration, for example, suppositories which consist of a combination of the active ingredient with a suppository base. Suitable suppository bases are, for example, natural or synthetic triglycerides, paraffin hydrocarbons, polyethylene glycols or higher alkanols. Gelatine rectal capsules which contain a combination of the active ingredient with a base may also be used; as bases there come into consideration, for example, liquid triglycerides, polyethylene glycols or paraffin hydrocarbons.

Especially suitable for parenteral administration are aqueous solutions of an active ingredient in water-soluble form, for example solutions of a water-soluble salt, and also suspensions of the active ingredient, such as corresponding oily injection suspensions, with suitable lipophilic solvents or vehicles, such as fatty oils, for example sesame oil, or synthetic fatty acid esters, for example ethyl oleate, or triglycerides being used, or aqueous injection suspensions containing substances that increase the viscosity, for example sodium carboxymethylcellulose, sorbitol and/or dextran, and, optionally, stabilisers.

The pharmaceutical preparations of the present invention can be produced in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture and, if desired or necessary after the addition of suitable adjuncts, processing the mixture or granulate to form tablets or dragée cores.

The following Examples illustrate the invention described above without limiting the scope thereof in any way. Temperatures are given in degrees Centigrade.

EXAMPLE 1

51 ml of triethylamine and 34 ml of chloroformic acid ethyl ester are added dropwise in succession, at $-10°$, to a solution of 30 g of crotonic acid in 1500 ml of methylene chloride. After 20 minutes, there is added at this temperature a suspension of 153 g of 1-[4-(2-aminoethyl)-phenylsulphonyl]-2-imino-3-cyclohexylimidazolidine dihydrochloride in 1500 ml of methylene chloride and, at 0°, a solution of 107 ml of triethylamine in 500 ml of methylene chloride is added dropwise. The whole is stirred for a further 3 hours at 0° and for 12 hours at room temperature, the solution becoming clear. It is washed in succession with 500 ml each of water, saturated aqueous sodium bicarbonate solution and water. The organic phase is dried over sodium sulphate, filtered and concentrated to dryness by evaporation under reduced pressure. The resulting 1-{4-[2-(crotonylamino)-ethyl]-phenylsulphonyl}-3-cyclohexyl-2-imino-imidazolidine (trans) is recrystallised from ethyl acetate and melts at 157° to 158°.

EXAMPLE 2

A solution of 1.5 g of crotonic acid anhydride in 5 ml of absolute dioxan is added dropwise at 0° to a solution of 3.5 g of 1-[4-(2-aminoethyl)-phenylsulphonyl]-2-imino-3-cyclohexylimidazolidine in 100 ml of absolute dioxan. After stirring for 12 hours at room temperature, the dioxan is distilled off, the residue is dissolved in 300 ml of methylene chloride, and the solution is washed in succession with 50 ml each of water, 0.5N aqueous sodium hydroxide and water. The organic phase is dried over sodium sulphate, filtered and concentrated to dryness by evaporation under reduced pressure. There is thus obtained 1-{4-[2-(crotonylamino)-ethyl]-phenylsulphonyl}-3-cyclohexyl-2-imino-imidazolidine (trans) which, when recrystallised from ethyl acetate, melts at 157° to 158°.

EXAMPLE 3

2.7 g of triethylamine, 2.7 g of chloroformic acid ethyl ester and a solution of 7.4 g of 1-[4-(2-aminoethyl)-phenylsulphonyl]-2-imino-3-cyclohexylimidazolidine in 100 ml of methylene chloride are added in succession, at −10°, to a solution of 2.2 g of vinylacetic acid. After stirring for 3 hours at 0°, the reaction mixture is left to stand overnight and is then washed in succession with water, saturated aqueous sodium bicarbonate solution and water. After recrystallisation from ethyl acetate, 1-{4-[2-(crotonylamino)-ethyl]-phenylsulphonyl}-3-cyclohexyl-2-imino-imidazolidine (trans), m.p. 157° to 158°, is obtained.

EXAMPLE 4

20.4 g of 1-cyclohexyl-2-imino-imidazolidine hydrochloride are added to 8.5 g of sodium hydroxide in 85 ml of water. There is added to the resulting solution 28.8 g of 4-(2-crotonylaminoethyl)-benzenesulphonyl chloride dissolved in 100 ml of acetone, the reaction mixture becoming warm. It is heated at 90° for half an hour and then concentrated by evaporation under reduced pressure. The residue is recrystallised from ethyl acetate, and 1-{4-[2-(crotonylamino)-ethyl]-phenylsulphonyl}-3-cyclohexyl-2-imino-imidazolidine (trans) which melts at 157° to 158° is obtained.

The starting material can be manufactured as follows:

18.9 g of N-(2-phenethyl)-crotonic acid amide are added in portions, while stirring, to 35.0 g of chlorosulfonic acid. The mixture is then stirred for 3 hours at 60°, whereupon it is poured onto ice. The crystals are filtered with suction, washed with water and dried under reduced pressure. The resulting 4-(2-crotonylaminoethyl)-benzenesulphonyl chloride is further processed in the form of the crude product.

EXAMPLE 5

A mixture of 28 ml of 4N aqueous sodium hydroxide solution and 4.3 g of ethyleneimine is cooled to −10°. A suspension of 28.8 g of 4-(2-crotonylaminoethyl)-benzenesulphonyl chloride in 100 ml of acetone is then added while stirring and cooling, so that the temperature does not exceed 0°. When the dropwise addition is complete, stirring is continued for 30 minutes at 0°. The cooling bath is then removed and there is added to the solution of the resulting 1-[4-(2-crotonylaminoethyl)-phenylsulphonyl]-aziridine 100 ml of cyclohexylamine. The temperature increases to 40°-50°. The reaction mixture is stirred for a further hour and the excess amine is then distilled off in a rotary evaporator. The resulting crystal mass which contains, in addition to sodium chloride, the desired 1-[4-(2-crotonylaminoethyl)-phenylsulphonyl]-2-cyclohexylethylenediamine is dissolved in 56 ml of 2N aqueous sodium hydroxide, and 10.6 g of cyanogen bromide are added thereto in portions while stirring, the temperature not being allowed to exceed 40°. After one hour, extraction is carried out with methylene chloride, and the organic solution is washed with 20 ml of 2N aqueous sodium hydroxide and twice with 100 ml of water. After drying the methylene chloride solution and concentrating it by evaporation under reduced pressure, the residue is recrystallised from ethyl acetate and yields 1-{4-[2-(crotonylamino)-ethyl]-phenylsulphonyl}-3-cyclohexyl-2-imino-imidazolidine (trans) of melting point 157° to 158°.

EXAMPLE 6

A solution of 19.8 g of cyclohexylamine in 400 ml of absolute diethyl ether is added dropwise at −5° to a solution of 10.6 g of cyanogen bromide in 100 ml of absolute diethyl ether. When the addition is complete, the whole is stirred for 30 minutes, the cyclohexylamine hydrobromide which has precipitated is filtered off and, at −5° with the exclusion of moisture, 5.3 g of a 50% suspension of sodium hydride in mineral oil are introduced in portions into the filtrate. When the addition is complete, the mixture is stirred for a further 30 minutes at −5° and the temperature is then allowed to increase to 20°. There is then added dropwise to the resulting suspension of sodium cyclohexylcyanamide, in the course of 15 minutes, a solution of 33.1 g of N-(2-chloroethyl)-4-(2-crotonylaminoethyl)-benzenesulphonamide in 100 ml of dioxan, and the resulting suspension is stirred for 15 hours at room temperature and then refluxed for 5 hours. After cooling to room temperature, 100 ml of water are added thereto and the whole is concentrated to dryness by evaporation under reduced pressure. The residue is partitioned between water and chloroform, the insoluble portion is filtered off, and the two phases are separated. The chloroform phase is extracted with 2N hydrochloric acid, and, while cooling, the aqueous-acidic extract is rendered alkaline with concentrated aqueous sodium hydroxide and extracted with methylene chloride. The methylene chloride extract is dried with sodium sulphate and the methylene chloride is distilled off. The residue is recrystallised from ethyl acetate and yields 1-{4-[2-(crotonylamino)-ethyl]-phenylsulphonyl}-3-cyclohexyl-2-imino-imidazolidine (trans) which melts at 157° to 158°.

EXAMPLE 7

A solution of 28.8 g of 4-(2-crotonylaminoethyl)-benzenesulphonyl chloride in 100 ml of acetone is added dropwise to a solution of 8.0 g of sodium hydroxide and 4.3 g of ethyleneimine in 60 ml of water, the temperature of the mixture being maintained between 0° and +10° by cooling. When the addition is complete, stirring is carried out for one hour at room temperature and then the acetone is evaporated off under reduced pressure. Crude N-[4-(2-crotonylaminoethyl)-phenylsulphonyl]-ethyleneimine separates from the remaining aqueous solution in the form of an oil. It is extracted with methylene chloride, the extract is dried with sodium sulphate and the methylene chloride is evaporated off under reduced pressure. N-[4-(2-crotonylaminoethyl)-phenylsulphonyl]-ethyleneimine remains behind as a crystalline residue.

A solution of 10.6 g of cyanogen bromide in 100 ml of absolute diethyl ether is added dropwise, while stirring at −5°, to a solution of 19.8 g of cyclohexylamine in 400 ml of absolute diethyl ether. After 30 minutes, the cyclohexylamine hydrobromide which has precipitated is filtered off, and 5.3 g of a sodium hydride-mineral oil suspension (50% strength) are added in portions, at −5°, to the filtrate. Stirring is continued for a further 30 minutes at −5° and the temperature is then allowed to increase to approximately 20°. Into the resulting, white suspension of sodium cyclohexyl-cyanamide there is then introduced, while stirring, a solution of the N-[4-(2-crotonylaminoethyl)-phenylsulphonyl]-ethyleneimine prepared according to the above process, in 150 ml of dioxan. The resulting suspension is stirred for 15 hours at room temperature and then refluxed for 5 hours. After cooling to room temperature, 50 ml of water are added dropwise thereto and the whole is concentrated to dryness by evaporation under reduced pressure. The residue is partitioned between chloroform and concentrated aqueous sodium hydroxide. The chloroform phase is decanted from the insoluble resins, extracted with 2N hydrochloric acid, and the extract is rendered alkaline with concentrated aqueous sodium hydroxide and extracted with methylene chloride. The organic phase is dried over sodium sulphate, filtered and concentrated to dryness by evaporation under reduced pressure. The 1-{4-[2-(crotonylamino)-ethyl]-phenylsulphonyl}-3-cyclohexyl-2-imino-imidazolidine (trans) which remains is recrystallised from ethyl acetate and melts at 157° to 158°.

EXAMPLE 8

26.8 g of 4-(2-crotonylaminoethyl)-benzenesulphonamide and 18.7 g of N-(2-chloroethyl)-N-cyclohexyl-cyanamide are added to a mixture of 4 g of sodium hydroxide, 15 ml of water and 300 ml of dimethyl sulphoxide. The resulting solution is heated for 1 hour at a bath temperature of 110°. The dimethyl sulphoxide is distilled off under reduced pressure and the residue, a brown oil, is taken up in methylene chloride. The organic phase is washed three times with water, dried and filtered and yields, after concentration by evaporation under reduced pressure, a brown crystalline residue. After recrystallisation from ethyl acetate, 1-{4-[2-(crotonylamino)-ethyl]-phenylsulphonyl}-3-cyclohexyl-2-imino-imidazolidine (trans) of melting point 157° to 158° is obtained.

EXAMPLE 9

To a solution of 9.0 g of disodium cyanamide in 50 ml of water there are added, first of all, 15 ml of acetone and then, in portions, in the course of 15 minutes, 29.8 g of 4-(2-crotonylaminoethyl)-benzenesulphonyl chloride. Thereupon, 19.8 g of 2-chloroethylcyclohexylamine hydrochloride are added and the whole is concentrated to dryness by evaporation. The paste-like residue is extracted with a mixture of 150 ml of ethanol and 150 ml of isopropanol. The extract is concentrated to dryness by evaporation under reduced pressure, the residue is taken up in 200 ml of acetone, the solution is filtered and the filtrate is again concentrated by evaporation. The remaining, clear, yellow oil is heated for 10 hours at 145°. The vitreous residue which is left behind after cooling is taken up in water and acidified with 2N hydrochloric acid, and the solution is washed with chloroform. The aqueous phase is then rendered alkaline with concentrated aqueous sodium hydroxide while cooling, during which an oil separates which is taken up in methylene chloride. The resulting methylene chloride solution is washed with water, dried over sodium sulphate and then concentrated to dryness by evaporation under reduced pressure. Upon subsequently chromatographing the residue over silica gel there is eluted with chloroform containing 2.5% methanol 1-{4-[2-(crotonylamino)-ethyl]-phenylsulphonyl}-3-cyclohexyl-2-imino-imidazolidine (trans) which crystallises after evaporating the solvent and, after being recrystallised from ethyl acetate, melts at 157° to 158°.

EXAMPLE 10

2 g of isocrotonic acid are dissolved in 100 ml of methylene chloride. At −10°, 3.4 ml of triethylamine, 2.4 ml of chloroformic acid ethyl ester and, after 20 minutes, a solution of 10.2 g of 1-[4-(2-aminoethyl)-phenylsulphonyl]-2-imino-3-cyclohexylimidazolidine in 100 ml of methylene chloride are added dropwise. The reaction mixture is left for 3 hours at 0° and for 12 hours at room temperature, then diluted with methylene chloride and washed in succession with water, a saturated aqueous sodium bicarbonate solution and water. The organic phase is dried over sodium sulphate, filtered and concentrated by evaporation under reduced pressure. The oil which remains is crystallised with petroleum ether and the resulting 3-cyclohexyl-2-imino-1-{4-[2-(isocrotonylamino)-ethyl]-phenylsulphonyl}-imidazolidine (cis) is recrystallised from ethyl acetate. M.p. 93° to 94°.

EXAMPLE 11

3.4 ml of triethylamine, 2.4 ml of chloroformic acid ethyl ester, a suspension of 10.2 g of 1-[4-(2-aminoethyl)-phenylsulphonyl]-2-imino-3-cyclohexylimidazolidine dihydrochloride in 100 ml of methylene chloride and again 7 ml of triethylamine in 100 ml of methylene chloride are added dropwise in succession, at −10°, to a solution of 2.4 g of tiglic acid in 100 ml of methylene chloride. The reaction mixture is allowed to warm up slowly to room temperature and is stirred for a further 12 hours. The reaction mixture is then washed with water, a saturated aqueous sodium bicarbonate solution and water. After drying the organic phase over sodium sulphate, concentration by evaporation under reduced pressure is carried out and the oil which remains is recrystallised from ethyl acetate. There is thus obtained 3-cyclohexyl-2-imino-1-{4-[2-(2,3-dimethylacrylamino)-ethyl]-phenylsulphonyl}-imidazolidine (trans) of melting point 140° to 142°.

EXAMPLE 12

3.4 ml of triethylamine and 2.4 ml of chloroformic acid ethyl ester are added dropwise, at −10°, to a solution of 2.8 g of trans 4-methyl-2-pentenoic acid in 100 ml of methylene chloride and, after 30 minutes, a solution of 8.4 g of 1-[4-(2-aminoethyl)-phenylsulphonyl]-2-imino-3-cyclohexylimidazolidine in 100 ml of methylene chloride is added dropwise and the whole is stirred for 3 hours at 0° and for 12 hours at room temperature. After filtration, the filtrate is washed with 50 ml each of water, a saturated aqueous sodium bicarbonate solution and water, dried over sodium sulphate, filtered again and concentrated by evaporation under reduced pressure. The resulting 3-cyclohexyl-2-imino-1-{4-[2-(4-methyl-2-pentenoylamino)-ethyl]-phenylsulphonyl}-2-imino-3-cyclohexylimidazolidine (trans) is recrystallised from ethyl acetate. M.p. 160° to 162°.

EXAMPLE 13

3.4 ml of triethylamine and 2.4 ml of chloroformic acid ethyl ester are added dropwise at −10° to a solution of 2.7 g of trans-2-hexenoic acid in 100 ml of methylene chloride. After 20 minutes, a suspension of 10.2 g of 1-[4-(2-aminoethyl)-phenylsulphonyl]-2-imino-3-cyclohexylimidazolidine dihydrochloride in 100 ml of methylene chloride and a solution of 5 g of triethylamine in 100 ml of methylene chloride are added dropwise at 0°. The whole is left to react for 3 hours at 0° and for 12 hours at room temperature, and the reaction mixture is washed with water, dried over magnesium sulphate, filtered and concentrated by evaporation under reduced pressure. The white, crystalline residue is recrystallised from ethyl acetate. The 3-cyclohexyl-2-imino-1-{4-[2-(2-hexenoylamino)-ethyl]-phenylsulphonyl}-imidazolidine (trans) obtainable in this manner then melts at 153° to 156°.

EXAMPLE 14

Tablets, each containing 100 mg of 1-{4-[2-(crotonylamino)-ethyl]-phenylsulphonyl}-3-cyclohexyl-2-imino-imidazolidine (trans), can be prepared as follows:

| Composition (for 10,000 tablets): | |
|---|---|
| 1-{4-[2-(crotonylamino)-ethyl]-phenyl-sulphonyl}-3-cyclohexyl-2-imino-imidazolidine (trans) | 1000.0 g |
| lactose | 500.0 g |
| potato starch | 330.0 g |
| gelatine | 8.0 g |
| talc | 60.0 g |
| magnesium stearate | 10.0 g |
| silica (colloidal) | 20.0 g |
| water | q.s. |

The 1-{4-[2-(crotonylamino)-ethyl]-phenylsulphonyl}-3-cyclohexyl-2-imino-imidazolidine (trans) is mixed with the lactose and 270.0 g of the potato starch, the mixture is moistened with an aqueous solution of the gelatine and granulated through a sieve. After drying, the remainder of the potato starch, the talc, the magnesium stearate and the colloidal silica are mixed in and the mixture is pressed to form tablets weighing 200 mg which may, if desired, be provided with dividing notches for finer adjustment of the dosage.

EXAMPLE 15

Dragées, each consisting 100 mg of 1-{4-[2-(crotonyl-amino)-ethyl]-phenylsulphonyl}-3-cyclohexyl-2-imino-imidazolidine (trans), can be prepared as follows:

| Composition (for 10,000 dragees): | |
|---|---|
| 1-{4-[2-(crotonylamino)-ethyl]-phenyl-sulphonyl}-3-cyclohexyl-2-imino-imidazolidine (trans) | 1000.0 g |
| lactose | 500.0 g |
| silica (colloidal) | 290.0 g |
| talc | 290.0 g |
| potato starch | 40.0 g |
| magnesium stearate | 5.0 g |
| saccharose (cryst.) | 533.0 g |
| shellac | 20.0 g |
| gum arabic | 75.0 g |
| dye | 1.5 g |
| Composition (for 10,000 dragees): | |
| water | q.s. |

The 1-{4-[2-(crotonylamino)-ethyl]-phenylsulphonyl}-3-cyclohexyl-2-imino-imidazolidine (trans) is mixed with the lactose and 270.0 g of the silica, 40.0 g of the talc, the potato starch and the magnesium stearate and pressed to form dragée cores. These are then coated with a concentrated aqueous syrup consisting of the saccharose, shellac, gum arabic, the remainder of the talc and silica and the dye and dried. The resulting dragées have a weight of 240 mg.

I claim:

1. A compound of the formula

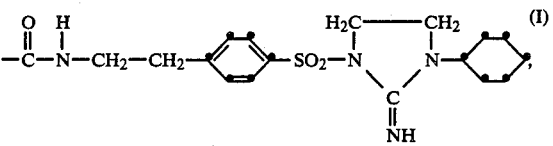

in which R represents the radical of the formula

in which

R$_1$ represents alkyl having up to 3 carbon atoms and each of R$_2$ and R$_3$, independently of the other, represents hydrogen or methyl, or a pharmaceutically acceptable salt of such a compound.

2. 1-{4-[2-(crotonylamino)-ethyl]-phenylsulphonyl}-3-cyclohexyl-2-imino-imidazolidine according to claim 1.

3. 3-cyclohexyl-2-imino-1-}4-[2-(isocrotonylamino)-ethyl]-phenylsulphonyl}-imidazolidine according to claim 1.

4. 3-cyclohexyl-2-imino-1-{4-[2-(2,3-dimethylacrylamido)-ethyl]-phenylsulphonyl}-imidazolidine (trans) according to claim 1.

5. 3-cyclohexyl-2-imino-1-{4-[2-(4-methyl-2-pentenoylamino)-ethyl]-phenylsulphonyl}-2-imino-3-cyclohexylimidazolidine (trans) according to claim 1.

6. 3-cyclohexyl-2-imino-1-{4-[2-(2-hexenoylamino)-ethyl]-phenylsulphonyl}-imidazolidine (trans) according to claim 1.

7. A pharmaceutical preparation containing an effective blood sugar reducing amount of a compound according to claim 1, and a pharmaceutically acceptable carrier.

8. A pharmaceutical preparation according to claim 7, wherein said compound is 1-{4-[2-(crotonylamino)-ethyl]-phenylsulfonyl}-3-cyclohexyl-2-imino-imidazolidine.

9. A method of treating diabetes in a mammal comprising administering to said mammal a therapeutically effective amount of a compound of the formula I according to claim 1.

* * * * *